United States Patent [19]

Ghedina

[11] Patent Number: 4,943,276
[45] Date of Patent: Jul. 24, 1990

[54] DEVICE FOR THE DISCHARGE OF INTESTINAL GASES

[76] Inventor: Dino Ghedina, Schillerstrabe 4, A-6020 Innsbruck, Austria

[21] Appl. No.: 366,314

[22] Filed: Jun. 13, 1989

Related U.S. Application Data

[63] Continuation of Ser. No. 64,884, Jun. 22, 1987, abandoned.

[30] Foreign Application Priority Data

Jul. 15, 1986 [AT] Austria .................................. 1917/86

[51] Int. Cl.$^5$ .............................................. A61B 19/00
[52] U.S. Cl. .............................. 600/29; 128/DIG. 25; 604/355
[58] Field of Search ............... 128/1 R, DIG. 25, 343; 604/338, 355; 600/29, 32

[56] References Cited

U.S. PATENT DOCUMENTS 2,018,322 10/1935 Savally ................................ 604/355
4,261,340 4/1981 Baumel et al. ....................... 128/1 R
4,846,784 7/1989 Haber ..................................... 600/29

FOREIGN PATENT DOCUMENTS 42659 11/1970 Fed. Rep. of Germany.
2747245 4/1979 Fed. Rep. of Germany.

*Primary Examiner*—Jerome L. Kruter
*Attorney, Agent, or Firm*—Lorusso & Loud

[57] ABSTRACT

For the discharge of intestinal gases at reduced pressure, use is made of a cylindrical hollow body of flexible material, which is rounded at the insertion end and which is made up of a front part and a rear part. The side wall has gas intake openings and connected to the second end region of the hollow body for the outlet of gas is a flexible thin tube which reduces the outlet cross-section from the hollow body as far as possible and which leads to the exterior, as the small outside diameter of the tube permits the hollow body to be positioned beyond the spincter muscle. The tube preferably extends into the collecting space of the hollow body to close to the insertion end.

6 Claims, 2 Drawing Sheets

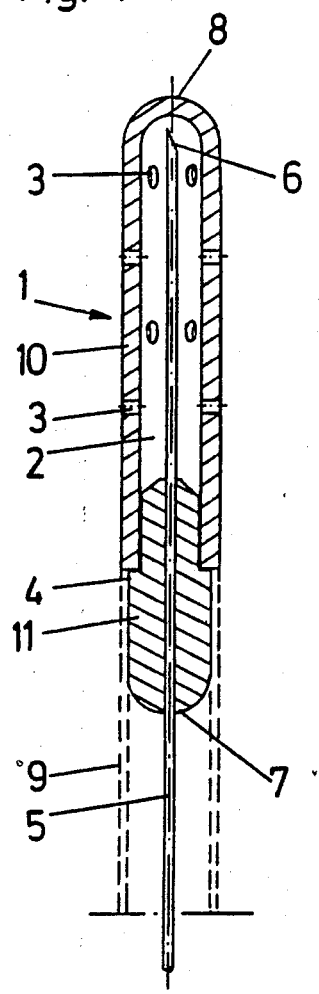
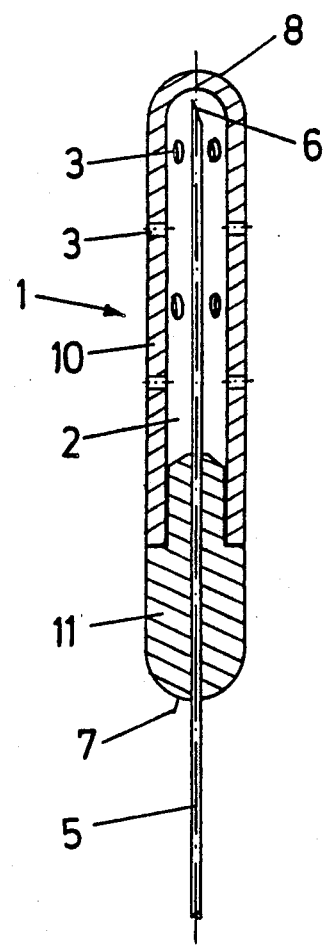
Fig. 1
Fig. 2

Fig. 3
Fig. 4
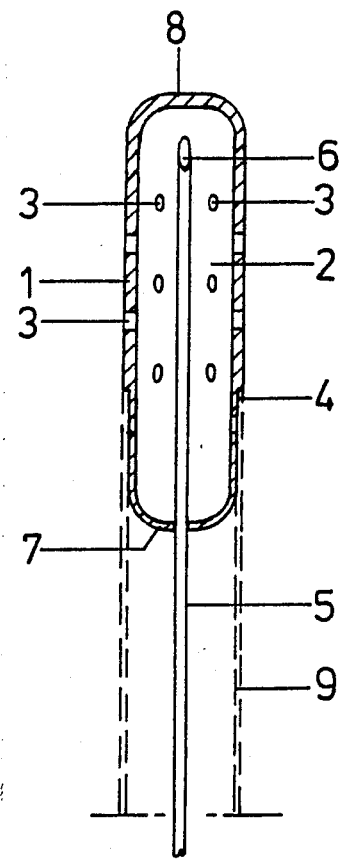
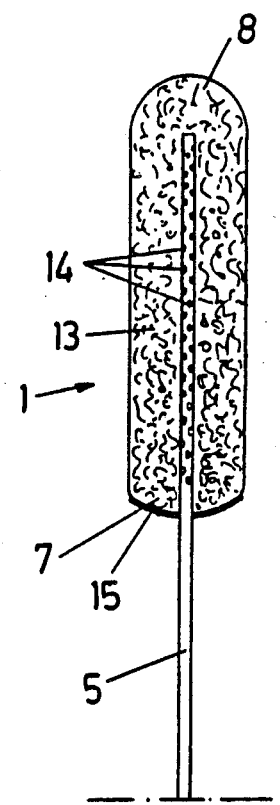

DEVICE FOR THE DISCHARGE OF INTESTINAL GASES

This is a continuation of co-pending application Ser. No. 07/064,884 filed on June 22, 1987, now abandoned.

BACKGROUND OF THE INVENTION

The invention relates to a device for the pressure-reduced discharge of intestinal gases comprising a hollow body of flexible material which has a rounded insertion end and whose wall is permeable to gas and in the second end region of which there is provided a gas outlet opening.

A device of that kind is to be found for example in German utility model No. 70 15 484. The hollow body described therein is provided with a flange for restricting the depth of insertion, whereby the sphincter muscle is constantly expanded by the hollow body so that use over a prolonged period of time is disagreeable. The inside diameter of the hollow body cannot therefore be excessively large, while however comparatively rapid filling with faeces also cannot be provided by the gas inlet openings being covered with bell-shaped lips. In addition there is the danger that the faeces can escape uncontrollably from the hollow body as it does not form a collecting space.

The invention is now based on the problem of avoiding the abovedescribed disadvantages and providing a device of the kind set forth in the opening part of this specification, which has substantially improved properties of use.

SUMMARY OF THE INVENTION

In accordance with the invention that is now solved in that a tube forming the gas outlet opening is sealingly connected to the second end region, the outside diameter of the tube being substantially smaller than that of the hollow body and the tube being of a length which permits positioning of the hollow body beyond the sphincter muscle.

The substantially smaller outside diameter of the tube provides for 'careful treatment' of the sphincter muscle which, after the hollow body has been set in position, embraces only the tube so that it is only expanded to the minimum degree. Tests have shown that there is no need also for particular features for retaining gas permeability as gas permeability generally suffers a reduction only after use over a prolonged period of time. Wearing times of several hours can thus be easily achieved. In order to provide for the transfer of gas from the hollow body into the tube for use over a prolonged period of time, a preferred embodiment provides that the tube extends into the interior of the hollow body. For example it may extend through the hollow body over almost the entire length thereof and may be chamfered at the end or may have circumferential openings in order to increase the inlet cross-section.

The small cross-section at the gas outlet end also gives the advantage that on the one hand it permits frequent discharge in very small amounts, in a noise-free manner due to the low pressure involved, while on the other hand there are no odour problems as the very small amounts which are discharged are very rapidly diluted by the outside air to such an extent that practically no odour can be detected.

A preferred embodiment of the invention may provide in particular that the hollow body is made up of two parts which are fitted one within the other, wherein the front part has the cap-shaped insertion end and gas inlet openings in the wall, while the rear part is provided with the tube.

In that embodiment the inside diameter of the hollow body may be made as large as possible in order to form a faeces collecting space of maximum volume without impeding the passage of gas therethrough.

Another embodiment provides that the hollow body comprises a porous material, in particular a filter cartridge, and the end portion of the tube which is enclosed by the filter cartridge has circumferential openings. That embodiment is primarily particularly simple to produce as the tube is only fitted into a suitable filter cartridge. The latter may comprise for example cellulose. In that connection it is advantageous for the end region of the filter cartridge, which is adjacent to the outwardly extending tube, to be impermeable to gas.

The tube which comprises flexible material preferably is of a stiffness which permits positioning of the device so that there is no need for an additional accessory for setting it in position.

It is also possible however for the hollow body or the rear part therefore to have a portion of reduced outside diameter, on to which is pushed a removable positioning tube member whose outside diameter corresponds to that of the hollow body or the front part thereof.

That tube member which serves as a positioning accessory is removed after the positioning operation and thrown away, while preferably, like the entire device, it comprises a rotable material which can be put into the sewerage system without causing problems. It will be appreciated that decomposition of the device should begin only after it has been in use for several hours.

The invention will now be described in greater detail with reference to the Figures of the accompanying drawings without however being restricted thereto. The drawings show views in longitudinal section through four different embodiments of the invention.

BRIEF DESCRIPTION OF THE DRAWING

FIG. 1 is a cross sectional view of one embodiment of the device of the present invention;

FIG. 2 is a cross sectional view of a second embodiment of the device of the present invention;

FIG. 3 is a cross sectional view of another embodiment of the device of the present invention; and FIG. 4 is a cross sectional view of a further embodiment of the present invention.

DETAILED DESCRIPTION OF THE INVENTION

FIGS. 1 to 3 show a cylindrical hollow body 1 of flexible material which is rounded at the impermeable insertion end 8 and which has a collecting space 2. Provided in the wall thereof are gas intake openings 3 which are distributed in any desired arrangement and through which the gases pass into the collecting space 2. The gases leave the hollow body 1 through a hose or tube 5 which is connected to the second end region 7. The outside diameter of the tube 5 is substantially reduced in comparison with that of the hollow body 1. The outlet cross-section is provided by the inside diameter of the tube 5 which is for example between 1 and 2 mm while the diameter of the collecting space 2 is for example from 8 to 10 mm in size. The tube 5 extends within the hollow body 1 to close to the rounded insertion end thereof and is provided with chamfer 6 at its end in order to increase the intake cross-section. The chamfer 6 is such that the elliptical intake cross-section is at least as large as the cross-section of an opening 3 in order as far as possible to prevent premature blockage of the tube 5 by material penetrating into the collecting space 2. The end of the tube 5 is preferably closer to the insertion end 8 than the foremost gas intake openings 3. The tube 5 is of a length which permits the hollow body 1 to be positioned in the space beyond the sphincter muscle so that only the thin tube 5 passes through the sphincter.

Referring to FIGS. 1 and 2, the hollow body 1 shown therein is made up of two parts 10 and 11 which are fitted one into the other. The front part 10 encloses the collecting space 2 and includes the openings 3. The rear part 11 serves as a closure plug and contains the tube 5 which extends into the collecting space 2. FIG. 3 shows a one-piece hollow body 1. The bending strength of the tube 5 is preferably such that it can be used as a positioning accessory. In that case, as shown in FIG. 2, the hollow body 1 is of a uniform outside diameter. As shown in FIGS. 1 and 3, it is also possible to use as a positioning accessory a positioning tube member 9 which is indicated in broken lines and which is withdrawn after insertion into the intestine. In that embodiment the desirable uniform outside diameter is achieved by virtue of a portion 4 of the rear part 11 (FIG. 1) or the hollow body 1 (FIG. 3) being reduced by the wall thickness of the positioning tube member 9, with the positioning tube member 9 being fitted on to the portion 4.

In the embodiment shown in FIG. 4 the hollow body 1 is formed by a filter cartridge 13 which is fitted on to the end portion of the tube 5. The filter cartridge 13 represents a porous gas-permeable body and may comprise for example fibrous cellulose or the like. The end portion of the tube 5 has a plurality of circumferential openings 14 through which the gases passing through the filter cartridge 13 pass into the tube 5. In this embodiment, the second end region 7 of the hollow body 1 is preferably of a gas-impermeable nature, for example being provided with a covering 15. In this embodiment, a positioning tube member as a positioning accessory could receive the entire filter cartridge 13.

I claim:

1. A device for the pressure-reduced discharge of intestinal gases consisting of:
   two opposed end portions, both of which have rounded end portions and a middle cylindrical wall portion, one end insertion portion and the middle portion being a void hollow portion for collecting gas and is of flexible material, the middle portion having a plurality of gas intake openings, said rounded one end portion being impermeable to gas;
   a second solid end portion securing a tube means;
   said gas collecting void positioned within said hollow wall and end portions into which gas passes through said plurality of gas intake openings;
   said tube means through which gas will exit the device located within said gas collecting void, the outside diameter of the tube means being substantially smaller than that of the gas collecting void and the tube means being of a sufficient length to extend from outside the second solid portion of the device into the interior of the gas collecting void to the area of the rounded gas-impermeable insertion end portion of the gas collecting void, said tube means being of a length which permits positioning of the second solid end portion beyond a sphincter muscle.

2. A device according to claim 1 characterized in that the device is made up of two parts, a front part and a rear part which are fitted one into the other, wherein the front part comprises the rounded insertion end portion impermeable to gas and the middle cylindrical wall portion including gas intake openings and the rear part is provided with the tube means.

3. A device according to claim 1 characterized in that the device is of an inside diameter from 8 to 10 mm and the tube means is of an inside diameter of from 1 to 1.5 mm.

4. A device according to claim 1 characterized in that the tube means is of a stiffness which permits positioning of the device.

5. A device according to claim 1 characterized in that the device or the rear part thereof has a portion of reduced outside diameter, on to which is fitted a removable positioning tube member whose outside diameter corresponds to that of the device or the front part thereof.

6. A device according to claim 1 characterized in that it comprises a material capable of decomposing.

* * * * *